(12) United States Patent
Terakawa

(10) Patent No.: US 10,010,245 B2
(45) Date of Patent: Jul. 3, 2018

(54) ENDOSCOPE SYSTEM, PROCESSOR DEVICE, AND METHOD FOR OPERATING ENDOSCOPE SYSTEM

(71) Applicant: FUJIFILM Corporation, Tokyo (JP)

(72) Inventor: Yuki Terakawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 947 days.

(21) Appl. No.: 14/471,591

(22) Filed: Aug. 28, 2014

(65) Prior Publication Data

US 2015/0080653 A1 Mar. 19, 2015

(30) Foreign Application Priority Data

Sep. 13, 2013 (JP) .................................. 2013-190568

(51) Int. Cl.
| | | |
|---|---|---|
| *A61B 1/00* | (2006.01) | |
| *A61B 1/04* | (2006.01) | |
| *A61B 1/06* | (2006.01) | |
| *G06T 5/50* | (2006.01) | |

(52) U.S. Cl.
CPC ........ *A61B 1/00186* (2013.01); *A61B 1/0005* (2013.01); *A61B 1/00009* (2013.01); *G06T 5/50* (2013.01); *G06T 2207/10024* (2013.01); *G06T 2207/10068* (2013.01); *G06T 2207/30101* (2013.01)

(58) Field of Classification Search
CPC ....... A61B 1/06; A61B 1/0638; A61B 1/0646; A61B 1/0653; A61B 1/043; A61B 1/00004; A61B 1/00009; A61B 1/0661; A61B 5/0059; A61B 5/0071; A61B 5/489

USPC ....... 600/109, 160, 177, 178, 180, 181, 476; 348/65, 68

See application file for complete search history.

(56) References Cited

U.S. PATENT DOCUMENTS

| | | | | |
|---|---|---|---|---|
| 2003/0071895 A1* | 4/2003 | Higuchi | ................. | H04N 7/183 348/65 |
| 2007/0024946 A1* | 2/2007 | Panasyuk | ............. | A61B 5/0059 359/253 |
| 2007/0225553 A1* | 9/2007 | Shahidi | .................. | A61B 5/064 600/103 |
| 2011/0077462 A1* | 3/2011 | Saitou | .................. | A61B 1/0638 600/109 |

(Continued)

*Primary Examiner* — Matthew J Kasztejna
*Assistant Examiner* — William Chou
(74) *Attorney, Agent, or Firm* — Birch, Stewart, Kolasch & Birch, LLP

(57) ABSTRACT

A subject irradiated with violet light and green light is imaged to obtain RGB signals, based on which a base image is produced. Frequency filtering processing is applied to the B signal to obtain a blood vessel extraction signal, in which a most superficial blood vessel, a superficial blood vessel, and a middle-layer blood vessel at different depths are extracted. Edge strength of each blood vessel in the blood vessel extraction signal is calculated. Display control processing based on the edge strength of each blood vessel is applied to the base image. Thereby, a first image or a second image is produced. In the first image, the most superficial blood vessel, the superficial blood vessel, and the middle-layer blood vessel are displayed in a distinguishable manner. In the second image, the most superficial blood vessel, the superficial blood vessel, and the middle-layer blood vessel are selectively enhanced or suppressed.

15 Claims, 14 Drawing Sheets

(56) References Cited

U.S. PATENT DOCUMENTS

2012/0197076 A1  8/2012  Minetoma

\* cited by examiner

ENDOSCOPE SYSTEM, PROCESSOR DEVICE, AND METHOD FOR OPERATING ENDOSCOPE SYSTEM

CROSS-REFERENCE TO RELATED APPLICATIONS

The present application claims priority under 35 U.S.C § 119 to Japanese Patent Application No. 2013-190568 filed on Sep. 13, 2013. The above application is hereby expressly incorporated by reference, in its entirety, into the present application.

BACKGROUND OF THE INVENTION

1. Field of the Invention

The present invention relates to an endoscope system, a processor device, and a method for operating an endoscope system, for enhancing structure of blood vessels and the like by use of narrowband light in observation.

2. Description Related to the Prior Art

In a medical field, diagnosis and treatment using an endoscope system, having a light source device, an endoscope, and a processor device, become widespread. For such diagnosis and treatment, normal observation and narrowband light observation are performed. In the normal observation, an observation object is imaged in its entirety by using broadband light such as white light. In the narrowband light observation, the structure of tissue such as blood vessels or ductal structure in the observation object is enhanced by using narrowband light having a specific narrow wavelength range.

In the narrowband light observation, both superficial blood vessels distributed in superficial tissue of the observation object and middle-layer blood vessels distributed in middle-to-deep tissue of the observation object are enhanced using blue narrowband light. However, there may be cases where the observation is focused only on the superficial blood vessels or the middle-layer blood vessels, depending on a purpose of diagnosis. In this case, it is desirable to enhance only one of the superficial blood vessel and the middle-layer blood vessel and suppress the other. According to U. S. Patent Application Publication No. 2012/0197076 (corresponding to Japanese Patent Laid-Open Publication No. 2012-152459), the superficial blood vessel or the middle-layer blood vessel is extracted from a B/G image, which has a luminance ratio B/G between a blue image having tissue information about the superficial tissue and a green image having tissue information about the middle-to-deep tissue. An image of the extracted blood vessel is superimposed on a base image, so that the superficial blood vessel and the middle-layer blood vessel are enhanced or suppressed selectively.

Of the blood vessels in the observation object, the superficial blood vessels are critical to the diagnosis. For the purpose of improving accuracy in diagnosis, it is desirable to display a superficial blood vessel, which is located deeper than a most superficial blood vessel, and the most superficial blood vessel, which is located in close vicinity to the surface of mucous membrane, in a distinguishable manner, and selectively enhance or suppress the blood vessels. However, in most cases, the blue image contains both of the most superficial blood vessel and the superficial blood vessel. It is difficult to extract the most superficial blood vessel and the superficial blood vessel independently from the B/G image described in the U.S. Patent Application Publication No. 2012/0197076, and hence to display the most superficial blood vessel and the superficial blood vessel separately or in a distinguishable manner.

SUMMARY OF THE INVENTION

An object of the present invention is to provide an endoscope system, a processor device, and a method for operating the endoscope, capable of displaying a most superficial blood vessel and a superficial blood vessel, which is located deeper than the most superficial blood vessel, in a distinguishable manner, and selectively enhancing or suppressing the blood vessels.

In order to achieve the above and other objects, the endoscope system of the present invention comprises an image signal generator, a base image generator, a frequency filtering processing unit, an edge strength calculator, and a special image generator. The image signal generator images a surface of mucous membrane of an observation object and produces color image signals composed of image signals of different colors. The base image generator produces a base image based on the color image signals. The frequency filtering processing unit applies frequency filtering processing to at least the image signal with a short wavelength of the color image signals and obtains a blood vessel extraction signal in which blood vessels at different depths are extracted. The edge strength calculator calculates edge strength of the each blood vessel based on the blood vessel extraction signal. The special image generator applies display control processing to the base image based on the edge strength of the each blood vessel and produces a special image in which a display of the each blood vessel is controlled.

It is preferable that the blood vessels in the blood vessel extraction signal include a first-layer blood vessel and a second-layer blood vessel located deeper than the first-layer blood vessel. In the blood vessel extraction signal, the first-layer blood vessel is represented by a falling edge with the edge strength exceeding a predetermined value. The second-layer blood vessel is represented by a falling edge with the edge strength less than or equal to the predetermined value.

It is preferable that the special image is a first special image in which one of the first-layer and second-layer blood vessels is represented by a falling edge and the other blood vessel is represented by a rising edge.

It is preferable that the first-layer blood vessel is represented by the falling edge and the second-layer blood vessel is represented by the rising edge in the first special image.

It is preferable that the special image generator includes a first display control image generator and an image superimposing unit. The first display control image generator produces a first display control image from the blood vessel extraction signal. The falling edge of the second-layer blood vessel is changed to a rising edge in the first display control image. The image superimposing unit adds the first display control image to the base image and changes a falling edge of the second-layer blood vessel in the base image to the rising edge and thereby produces the first special image.

It is preferable that the special image is a second special image in which the first-layer and second-layer blood vessels are selectively enhanced or suppressed.

It is preferable that the special image generator includes a second display control image generator and an image superimposing unit. The second display control image generator produces a second display control image based on the blood vessel extraction signal. An amount for enhancing or suppressing the each blood vessel is determined in accordance with the edge strength in the second display control image. The image superimposing unit superimposes the second display control image on the base image and produces the second special image.

It is preferable that the first-layer blood vessel is a most superficial blood vessel and the second-layer blood vessel is a superficial blood vessel or a middle-layer blood vessel.

It is preferable that the image signal with the short wavelength corresponds to violet light having a wavelength range of 380 to 440 nm.

It is preferable that the endoscope system further includes a violet light emitter for applying the violet light to the observation object. The image signal with the short wavelength is obtained by imaging the observation object under the violet light.

It is preferable that the endoscope system further includes a white light emitter and a spectral calculation unit. The white light emitter applies white light to the observation object. The spectral calculation unit performs spectral calculation based on a white light image of the observation object captured under the white light and thereby produces the image signal with the short wavelength.

It is preferable that the color image signals include the image signal with a long wavelength which corresponds to green light in a wavelength range of 480 to 600 nm or green narrowband light in a wavelength range of 530 to 550 nm. It is preferable that the base image is produced based on the image signal with the short wavelength and the image signal with the long wavelength.

The processor device of the present invention comprises a receiver, a base image generator, a frequency filtering processing unit, an edge strength calculator, and a special image generator. The receiver receives the color image signals. The base image generator produces a base image based on the color image signals. The frequency filtering processing unit applies frequency filtering processing to at least the image signal with a short wavelength of the color image signals and obtains a blood vessel extraction signal in which blood vessels at different depths are extracted. The edge strength calculator calculates edge strength of the each blood vessel based on the blood vessel extraction signal. The special image generator applies display control processing to the base image based on the edge strength of the each blood vessel and produces a special image in which a display of the each blood vessel is controlled. The processor device is connected to an endoscope having an image signal generator. The image signal generator images a surface of mucous membrane of an observation object to produce color image signals composed of image signals of different colors.

The method for operating an endoscope system according to the present invention comprises a color image signal producing step, a base image producing step, a blood vessel extraction signal obtaining step, an edge strength calculating step, and a special image producing step. In the color image signal producing step, an image signal generator images a surface of mucous membrane of an observation object and produces color image signals composed of image signals of different colors. In the base image producing step, a base image generator produces a base image based on the color image signals. In the blood vessel extraction signal obtaining step, a frequency filter processing unit applies frequency filtering processing to at least the image signal with a short wavelength of the color image signals and obtains a blood vessel extraction signal in which blood vessels at different depths are extracted. In the edge strength calculating step, an edge strength calculator calculates edge strength of the each blood vessel based on the blood vessel extraction signal. In the special image producing step, a special image generator applies display control processing to the base image based on the edge strength of the each blood vessel and produces a special image in which a display of the each blood vessel is controlled.

According to the present invention, the display control processing is performed in accordance with the edge strengths of the blood vessels of predetermined depths such as the most superficial blood vessel, the superficial blood vessel, and the middle-layer blood vessel. Thereby, the most superficial blood vessel, the superficial blood vessel, and the middle-layer blood vessel are displayed separately or in a distinguishable manner, and enhanced or suppressed selectively in the display.

BRIEF DESCRIPTION OF DRAWINGS

For more complete understanding of the present invention, and the advantage thereof, reference is now made to the subsequent descriptions taken in conjunction with the accompanying drawings, in which.

DESCRIPTION OF THE PREFERRED EMBODIMENTS (First Embodiment)

Figure 1:
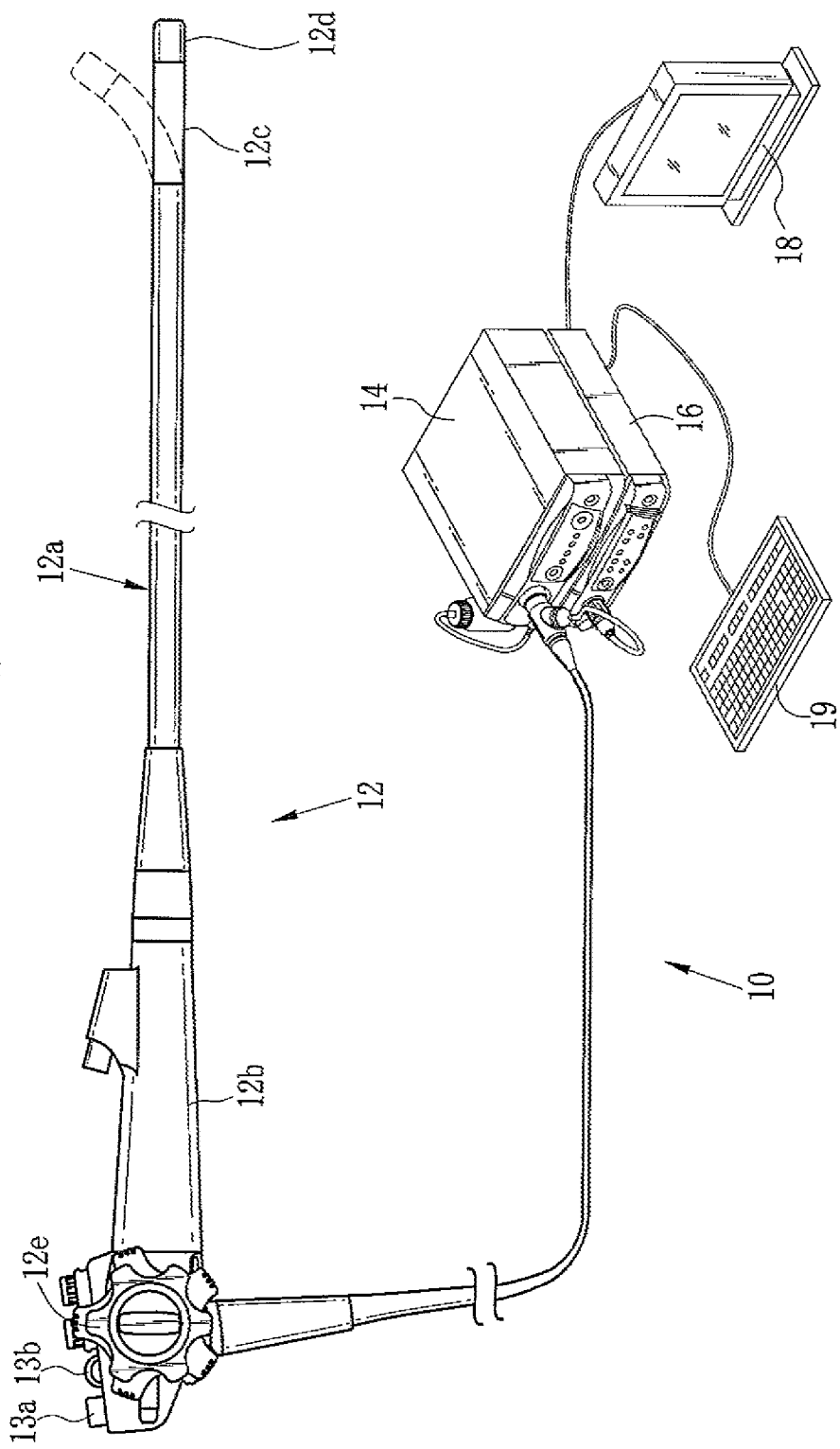
FIG. 1 is a schematic view of an endoscope system.

As shown in FIG. 1, an endoscope system 10 according to a first embodiment has an endoscope 12, a light source device 14, a processor device 16, a monitor 18, and a console 19. The endoscope 12 is connected optically to the light source device 14, and electrically to the processor device 16. The endoscope 12 has an insert section 12a to be introduced into a body cavity, a control handle unit 12b provided at a proximal end of the insert section 12a, a flexible assembly 12c provided at a tip end of the insert section 12a, and a head assembly 12d. Operating an angle knob 12e provided on the control handle unit 12b flexibly bends the flexible assembly 12c. The bending operation aims the head assembly 12d at a desired direction.

The control handle unit 12b is provided with a mode switch 13a and a zooming operation unit 13b, in addition to the angle knob 12e. The mode switch 13a is used for switching between two types of modes, that is, a normal observation mode and a special observation mode. In the normal observation mode, a normal image produced using white light is displayed on the monitor 18. In the special observation mode, a special image is displayed on the monitor 18. The special image is produced using light which makes contrast of a specific structure such as a superficial blood vessel different from that of mucous membrane and thereby enhances the specific structure in the special image. The special images include a first special image, in which a plurality of blood vessels in an observation object are displayed separately or in a distinguishable manner according to their depths, and a second special image, in which the plurality of blood vessels having certain depths in the observation object are selectively enhanced or suppressed. The zooming operation unit 13b is used for operating a zooming lens 47 (see FIG. 2). Moving the zooming lens 47 on a telephoto side magnifies the observation object. Note that, in the special observation mode, the console 19 is operated to choose which one of the first and second special images is displayed.

The processor device 16 is electrically connected to the monitor 18 and the console 19. The monitor 18 outputs and displays image information and the like. The console 19 functions as a UI (user interface) for receiving input of functional settings and the like. Note that an external storage (not shown) may be connected to the processor device 16 to store the image information and the like.

Figure 2:
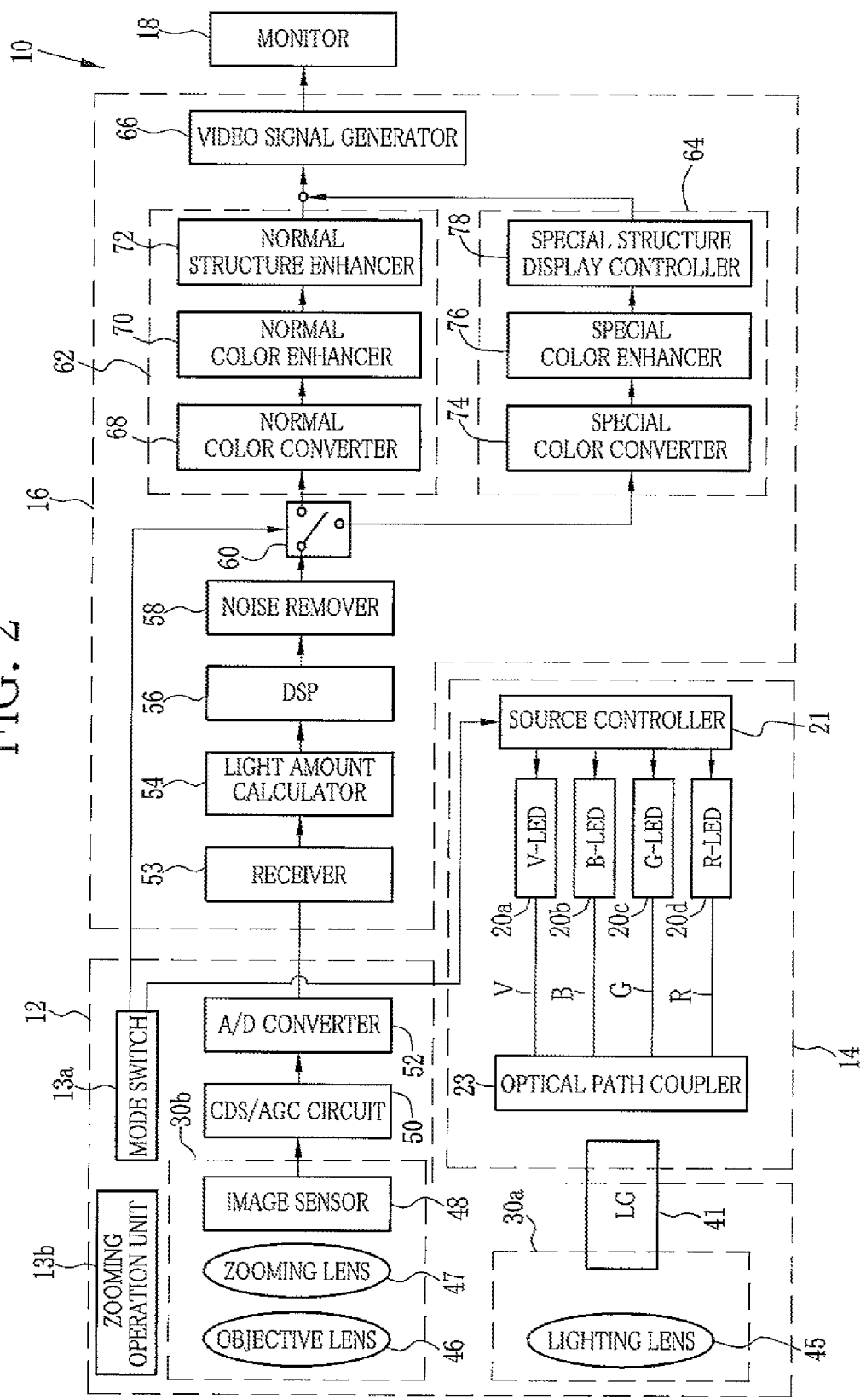
FIG. 2 is a functional block diagram of the endoscope system according to a first embodiment.

As shown in FIG. 2, the light source device 14 is provided with a V-LED (violet light emitting diode) 20a, a B-LED (blue light emitting diode) 20b, a G-LED (green light emitting diode) 20c, a R-LED (red light emitting diode) 20d, a source controller 21 for controlling the operation of the four LEDs, and an optical path coupler 23 for coupling optical paths of the four colors of light from the LEDs 20a to 20d. The light coupled by the optical path coupler 23 is applied to the observation object through a light guide 41, which extends through the insert section 12a, and a lighting lens 45. Note that a LD (laser diode) may be used instead of the LED.

The V-LED 20a emits violet light V having a center wavelength of 405 nm and a wavelength range of 380 to 440 nm. The B-LED 20b emits blue light B having a center wavelength of 460 nm and a wavelength range of 440 to 480 nm. The G-LED 20c emits green light G having normal distribution from 480 to 600 nm. The R-LED 20d emits red light R having a center wavelength of 620 to 630 nm and a wavelength range of 600 to 650 nm.

Figure 3:
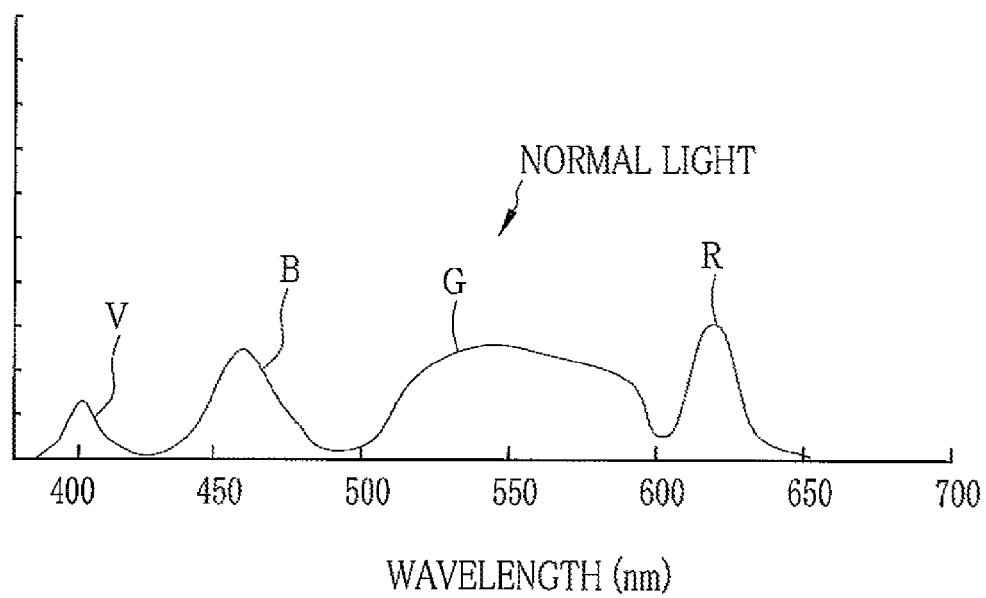
FIG. 3 is a graph showing an emission spectrum of normal light.
Figure 4:
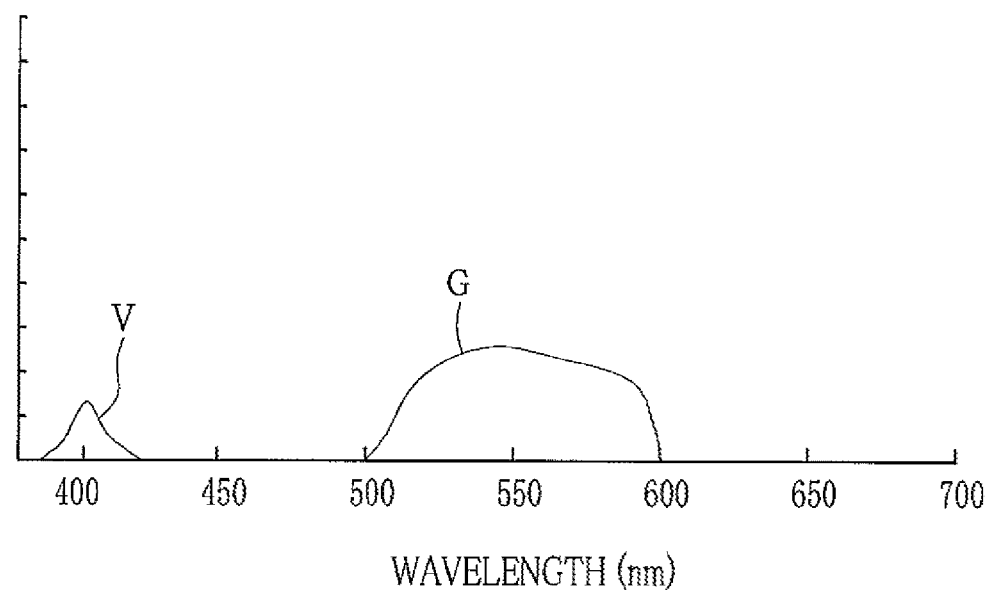
FIG. 4 is a graph showing emission spectrums of violet light V and green light G.

In the normal observation mode, the source controller 21 turns on all of the V-LED 20a, the B-LED 20b, the G-LED 20c, and the R-LED 20d. As shown in FIG. 3, mixing the four colors of light i.e. the violet light V, the blue light B, the green light G, and the red light R produces normal light. On the other hand, in the special observation mode, the V-LED 20a and the G-LED 20c are simultaneously turned on to emit the violet light V and the green light G at the same time. As shown in FIG. 4, the violet light V from the V-LED 20a and the green light G are generated at the same time.

As shown in FIG. 2, the light guide 41, which extends through a universal cord for connecting the light source device 14 and the endoscope 12, transmits the light coupled by the optical path coupler 23 to the head assembly 12d of the endoscope 12. Note that a multimode fiber is available as the light guide 41. By way of example, a small-diameter fiber cable having a core diameter of 105 μm, a clad diameter of 125 μm, and an outer diameter φ of 0.3 to 0.5 mm including a protective layer, being a jacket, is usable.

The head assembly 12d of the endoscope 12 contains a lighting optical system 30a and an imaging optical system 30b. The lighting optical system 30a has the lighting lens 45, through which the light transmitted through the light guide 41 is applied to the observation object. The imaging optical system 30b has an objective lens 46, the zooming lens 47, and an image sensor 48. The light reflected from the observation object is incident upon the image sensor 48 through the objective lens 46 and the zooming lens 47. A reflected image of the observation object is formed on the image sensor 48.

Figure 5:
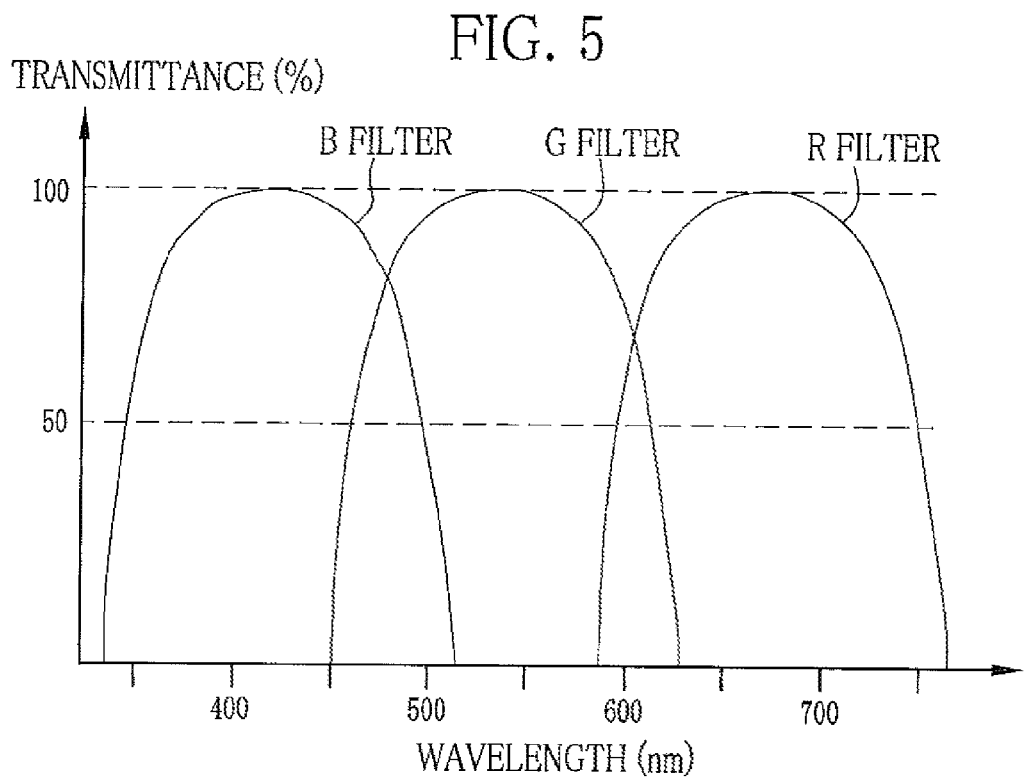
FIG. 5 is a graph showing spectral transmittance of a B filter, a G filter, and an R filter.

The image sensor 48 is a color imaging device, which captures the reflected image of the observation object and outputs an image signal. The image sensor 48 is preferably a CCD (charge coupled device) image sensor, a CMOS (complementary metal-oxide semiconductor) image sensor, or the like. The image sensor used in the present invention is a color image sensor for obtaining three-color image signals of R (red), G (green), and B (blue), that is, a so-called RGB image sensor having RGB filters in its imaging surface. As shown in FIG. 5, the B filter allows light of 340 to 520 nm to pass through. The G filter allows light of 450 to 630 nm to pass through. The R filter allows light of 580 to 770 nm to pass through. Accordingly, of the reflected light from the observation object, the violet light V passes through the B filter. The blue light B and the green light G pass through both the B filter and the G filter. The red light R passes through the R filter.

Figure 6:
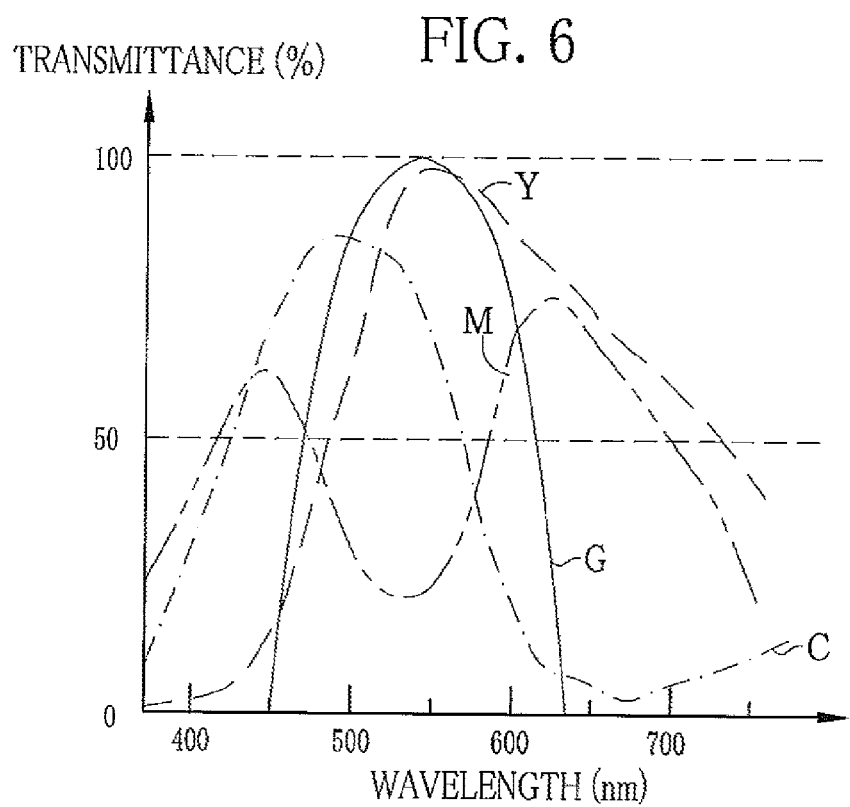
FIG. 6 is a graph showing spectral transmittance of complementary color filters of C (cyan), M (magenta), Y (yellow), and G (green)

Note that the image sensor 48 may be a so-called complementary color image sensor having complementary color filters of C (cyan), M (magenta), Y (yellow), and G (green) having spectral transmittance of FIG. 6. In the case of using the complementary color image sensor, the RGB three-color image signals are obtained by color conversion of CMYG four-color image signals. In this case, a color conversion means for making the color conversion from the CMYG four-color image signals into the RGB three-color image signals is necessary in at least one of the endoscope 12 and the processor device 16.

As shown in FIG. 2, the image signals outputted from the image sensor 48 are sent to a CDS/AGC circuit 50. The CDS/AGC circuit 50 applies correlated double sampling (CDS) and automatic gain control (AGC) to the image signals, being analog signals. The image signals subjected to the CDS and the AGC by the CDS/AGC circuit 50 are converted into digital image signals by an A/D (Analog/Digital) converter 52. The converted digital image signals are inputted to the processor device 16.

The processor device 16 is provided with a receiver 53, a light amount calculator 54, a digital signal processor (DSP) 56, a noise remover 58, an image processing switching unit 60, a normal image processing unit 62, a special image processing unit 64, and a video signal generator 66. The receiver 53 receives the digital RGB image signals from the endoscope 12. The R image signal corresponds to a signal outputted from R pixels (pixels having the R filters) of the image sensor 48. The G image signal corresponds to a signal outputted from G pixels (pixels having the G filters) of the image sensor 48. The B image signal corresponds to a signal outputted from B pixels (pixels having the B filters) of the image sensor 48.

The light amount calculator 54 calculates an exposure amount based on the digital RGB image signals received by the receiver 53, and calculates a target light amount to be used in the normal observation mode or the special observation mode based on the calculated exposure amount. The light amount calculator 54 produces a target light amount setting signal, which determines a target light amount of each LED 20*a* to 20*d*, based on the calculated target light amount and a set light amount ratio among the V-LED 20*a*, the B-LED 20*b*, the G-LED 20*c*, and the R-LED 20*d*.

In the normal observation mode, for example, the target light amount of the V-LED 20*a* is calculated by "P×(a/(a+b+c+d))" where "P" represents the light amount calculated by the light amount calculator 54 and the set light amount ratio is "V-LED:B-LED:G-LED:R-LED=a:b:c:d". The target light amount of the B-LED 20*b* is calculated by "P×(b/(a+b+c+d))". The target light amount of the G-LED 20*c* is calculated by "P×(c/(a+b+c+d))". The target light amount of the R-LED 20*d* is calculated by "P×(d/(a+b+c+d))". In the special observation mode, the target light amount of the V-LED 20*a* is calculated by "Q×(m/(m+n))" where "Q" represents the light amount calculated by the light amount calculator 54 and the set light amount ratio is "V-LED:G-LED=m:n". The target light amount of the G-LED 20*c* is calculated by "Q×(n/(m+n))". Note that the light amount ratio is set by the console 19 to different values between the normal observation mode and the special observation mode.

The DSP 56 applies gamma correction processing and color correction processing to the RGB image signals. The noise remover 58 applies noise removal processing (for example, by a method of moving averages, a median filter method, or the like) to the RGB image signals after the gamma correction and the like by the DSP 56. Thereby noise is removed from the RGB image signals. After the noise reduction, the RGB image signals are sent to the image processing switching unit 60.

The image processing switching unit 60 sends the RGB image signals to the normal image processing unit 62 in a case where the endoscope system 10 is put into the normal observation mode by operation of the mode switch 13*a*, and sends the RGB image signals to the special image processing unit 64 in a case where the endoscope system 10 is put into the special observation mode.

The normal image processing unit 62, having a normal color converter 68, a normal color enhancer 70, and a normal structure enhancer 72, produces a normal image in which the observation object is expressed in normal (actual) color of the tissue. The normal color converter 68 applies color conversion processing to the digital RGB image signals, and outputs the color-converted RGB image signals. Furthermore, the normal color converter 68 applies gradation conversion processing to the color-converted RGB image signals, and outputs the gradation-converted RGB image signals. The normal color enhancer 70 applies various types of color enhancement processing to the gradation-converted RGB image signals. The normal structure enhancer 72 applies structure enhancement processing, including sharpness processing, edge enhancement processing, and the like, to the color-enhanced RGB image signals. The RGB image signals, after being subjected to the structure enhancement processing by the normal structure enhancer 72, are inputted as the RGB image signals of the normal image to the video signal generator 66.

The special image processing unit 64 has a special color converter 74, a special color enhancer 76, and a special structure display controller 78. The special image processing unit 64 produces a first special image, in which most superficial blood vessels, superficial blood vessels, and middle-layer blood vessels are displayed separately or in a distinguishable manner, or a second special image, in which the most superficial blood vessels, superficial blood vessels, and the middle-layer blood vessels are selectively enhanced or suppressed. The depth from the surface of the mucous membrane to the most superficial blood vessel, the superficial blood vessel, and the middle-layer blood vessel increases in this order. The special color converter 74 applies color conversion processing to the digital RGB image signals, and outputs color-converted RGB image signals. In the special observation mode, the violet light V and the green light G, not detected by the R pixels but by the B pixels and the G pixels of the image sensor 48, are applied simultaneously to the observation object. Thus, the B image signal and the G image signal contain information, including information about the blood vessels and the like, about the observation object, while the R image signal hardly contains the information. For this reason, as represented by the following conversion expressions (1) to (3), the color conversion processing is performed based only on the B image signal and the G image signal, without using the R image signal.

Color-converted $R$ image signal=$k1 \times G$ image signal  (1)

Color-converted $G$ image signal=$k2 \times B$ image signal  (2)

Color-converted $B$ image signal=$k3 \times B$ image signal  (3)

Wherein, "k1" to "k3" are positive coefficients.

Furthermore, the special color converter 74 applies gradation conversion processing to the color-converted RGB image signals, and outputs the gradation-converted RGB image signals. The special color enhancer 76 applies various types of color enhancement processing to the gradation-converted RGB image signals. The special structure display controller 78 applies display control processing of the most superficial blood vessels, the superficial blood vessels, and the middle-layer blood vessels to the color-enhanced RGB image signals, as described in detail below. The RGB image signals, after being subjected to the display control processing by the special structure display controller 78, are inputted to the video signal generator 66.

Figure 7:
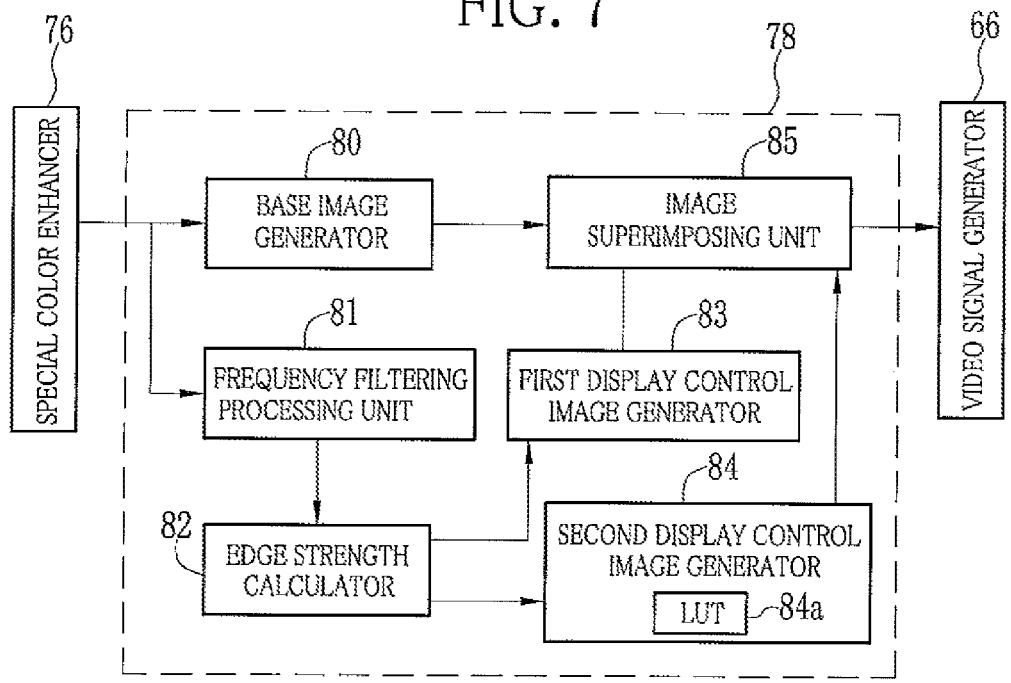
FIG. 7 is a block diagram showing the functions of a special structure display controller.

As shown in FIG. 7, the special structure display controller 78 includes a base image generator 80, a frequency filtering processing unit 81, an edge strength calculator 82, a first display control image generator 83, a second display control image generator 84, and an image superimposing unit 85. The RGB image signals, after being subjected to the color enhancement processing by the special color enhancer 76, are inputted to each of the base image generator 80 and the frequency filtering processing unit 81. Note that a special image generator of the present invention is constituted of the first display control image generator 83 and the image superimposing unit 85, or the second display control image generator 84 and the image superimposing unit 85.

Figure 8:
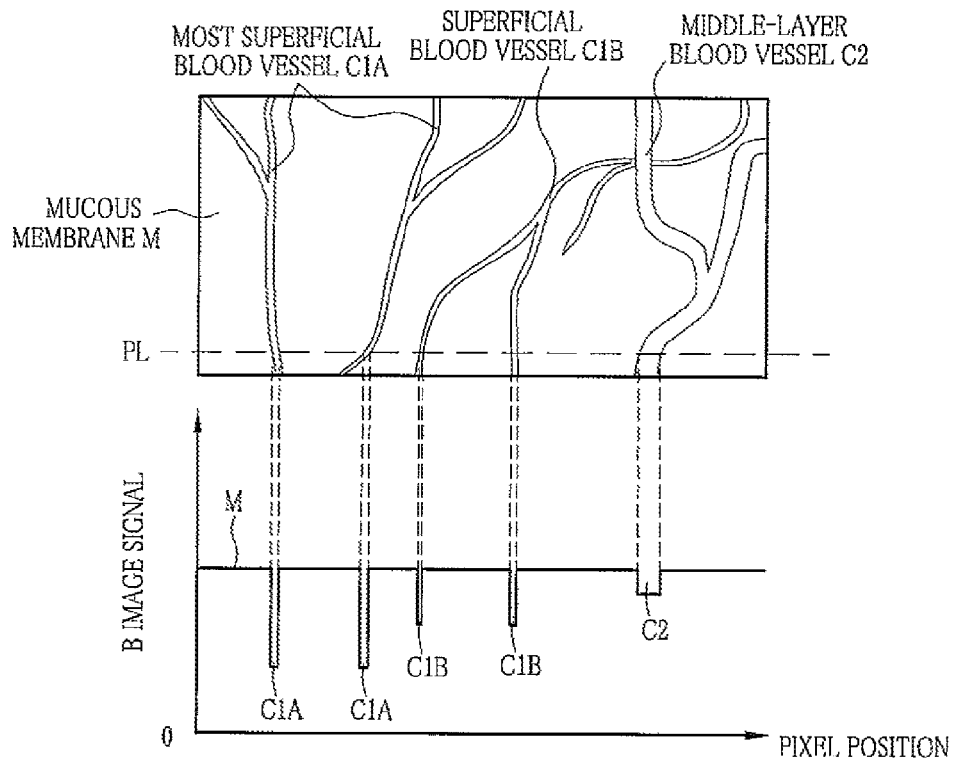
FIG. 8 is an explanatory view showing a color-enhanced B image signal (or a B image signal of a base image) and the signal distribution of the B image signal at a predetermined pixel line.

As shown in FIG. 8, of the color-enhanced RGB image signals, the B image signal has falling edges corresponding to most superficial blood vessels C1A, superficial blood vessels C1B, and a middle-layer blood vessel C2, which have lower pixel values than mucous membrane M, in a predetermined pixel line PL. Of the blood vessels which correspond to the falling edges, the most superficial blood vessels C1A have the lowest pixel values, the superficial blood vessels C1B have the second lowest pixel values, and the middle-layer blood vessel C2 has the highest pixel value. The G image signal of the color-enhanced RGB image signals has similar distribution to the B image signal, as shown in FIG. 8.

A pixel value decreases with decreasing depth of a blood vessel and thereby the contrast between the blood vessels and the mucous membrane M increases. The reason for this is as follows. Of the color-enhanced RGB image signals, the B image signal and the G image signal correspond to signals obtained by the color conversion processing (see the above conversion expressions (1) to (3)) of the B image signal, which is obtained by photoelectrically converting the violet light V with the B pixels of the image sensor 48. Hence, the pixel values of the B image signal and the G image signal at blood vessel portions are greatly influenced by the amount of light reflected from blood vessels irradiated with the violet light V. As shown in a simulation result in FIG. 9, the reflectance of a blood vessel for the violet light V, having a wavelength range of 380 to 440 nm, depends on a blood vessel depth d, which represents a distance from the surface of a mucous membrane to the blood vessel.

Figure 9:
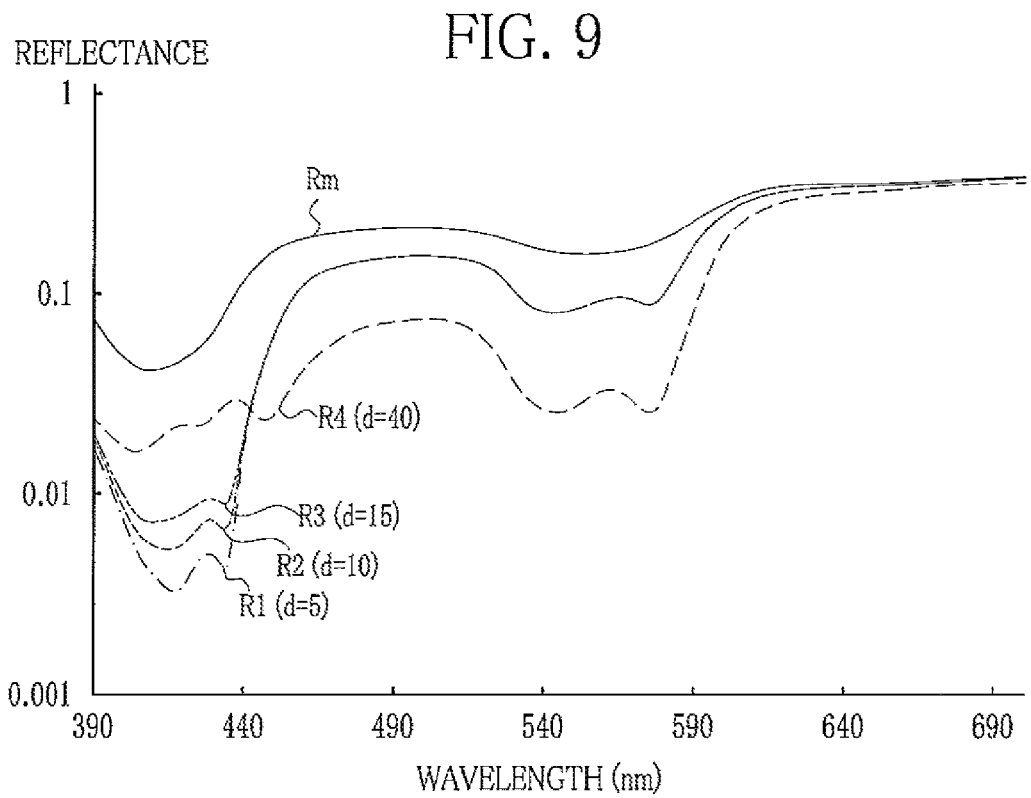
FIG. 9 is a graph showing spectral reflection spectrums of mucous membrane and a blood vessel, obtained by simulation, at predetermined depths.

FIG. 9 shows reflectances R1 to R3 of blood vessels having a diameter (thickness of the blood vessel) of 10 μm for light having a predetermined wavelength, and a reflectance R4 of a blood vessel having a diameter (thickness) of 40 μm for the light having the predetermined wavelength, in addition to a reflectance Rm of the mucous membrane M. "R1" represents the reflectance at a blood vessel depth d of 5 μm. "R2" represents the reflectance at a blood vessel depth d of 10 μm. "R3" represents the reflectance at a blood vessel depth d of 15 μm, and "R4" represents the reflectance at a blood vessel depth d of 40 μm. As shown in FIG. 9, it is apparent from the relation between the wavelength and the reflectance of the blood vessel that the reflectance of the blood vessel decreases with decreasing depth of the blood vessel and hence the pixel values, which correspond to the blood vessel, of the B and G image signals decrease with decreasing depth of the blood vessel, in a wavelength range of the violet light V, i.e. 380 to 440 nm. In other words, in the B image signal and the G image signal, the contrast between the blood vessel and the mucous membrane M increases with decreasing depth of the blood vessel.

Note that the fact "the pixel value corresponding to the blood vessel decreases with decreasing depth of the blood vessel" means that visible light having a wavelength range of 440 nm or less, such as the violet light V, provides resolving power for the blood vessel depths. On the contrary, as for light having a wavelength range of more than 440 nm, the pixel value corresponding to the blood vessel portion hardly changes even if the blood vessel depth decreases because the reflectance is almost the same at the blood vessel depth d in a range of 5 to 15 μm. Namely, the light having the wavelength range of more than 440 nm does not provide the resolving power for the blood vessel depth d within the range of 5 to 15 μm. Note that, in this embodiment, the most superficial blood vessel C1A is situated in a depth range from the approximate surface of the mucous membrane to 8 μm. The superficial blood vessel C1B is situated in a depth range approximately from 8 μm to 20 μm. The middle-layer blood vessel C2 is situated in a depth range from 20 μm to 45 μm. However, definition of the depth is not limited thereto.

Figure 10:
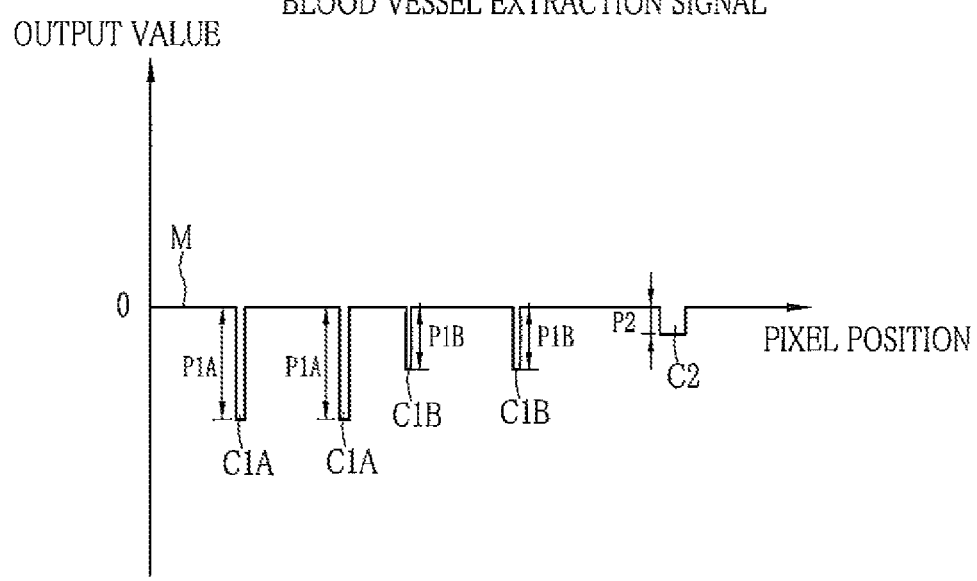
FIG. 10 is a graph showing the signal distribution of a blood vessel extraction signal at the predetermined pixel line.

The base image generator 80 produces a base image from the color-enhanced RGB image signals. The base image is composed of RGB image signals which correspond to the color-enhanced RGB image signals, respectively. The frequency filtering processing unit 81 applies frequency filtering processing to the color-enhanced B image signal. The frequency filtering processing is to extract frequency band components corresponding to the thicknesses of the most superficial blood vessel C1A, the superficial blood vessel C1B, and the middle-layer blood vessel C2, respectively. As shown in FIG. 10, applying the frequency filtering process to the B image signal allows obtainment of a blood vessel extraction signal, which has negative output values at portions corresponding to the most superficial blood vessels C1A, the superficial blood vessels C1B, and the middle-layer blood vessel C2, and an output value "0" at a portion corresponding to the mucous membrane M. Note that the frequency filtering processing unit 81 may apply the frequency filtering processing to both of the B image signal and the G image signal.

The edge strength calculator 82 calculates an edge strength of each blood vessel contained in the blood vessel extraction signal. Since the blood vessel extraction signal is obtained by applying the frequency filtering processing to the B image signal and the G image signal, in which pixel values decrease with decreasing blood vessel depth, as described above, an absolute value of the output value increases with decreasing blood vessel depth. In other words, the contrast between the blood vessel and the mucous membrane M increases with decreasing blood vessel depth and thereby the edge strength increases. Hence, as shown in FIG. 10, of the edge strengths calculated by the edge strength calculator 82, the most superficial blood vessel C1A has the highest edge strength P1A. The superficial blood vessel C1B has the second highest edge strength P1B. The middle-layer blood vessel C2 has the lowest edge strength P2 (P1A>P1B>P2).

The first display control image generator 83 produces a first display control image from the blood vessel extraction signal. The first display control image is used for displaying the most superficial blood vessel C1A, the superficial blood vessel C1B, and the middle-layer blood vessel C2 separately or in a distinguishable manner. The first display control image generator 83 changes the falling edge of the blood vessel having an edge strength of P1B or less into a rising edge, and increases an output value of the rising edge so that the blood vessel is made brighter than the mucous membrane in an image which is obtained by superimposing the first display control image on the base image. The blood vessel having an edge strength of more than P1B is maintained as the falling edge. Thus, the first display control image is obtained. Taking the case of a first display control image of FIG. 11 as an example, the most superficial blood vessels C1A are not changed into rising edges because an edge strength P1A exceeds P1B, being a threshold value. On the contrary, as for the superficial blood vessels C1B and the middle-layer blood vessel C2 whose edge strengths P1B and P2 are less than or equal to the threshold value P1B, the falling edges of the superficial blood vessels C1B and the middle-layer blood vessel C2 are changed into rising edges, and output values of the rising edges are increased by multiplying a predetermined coefficient to the original output values thereof.

Figure 12:
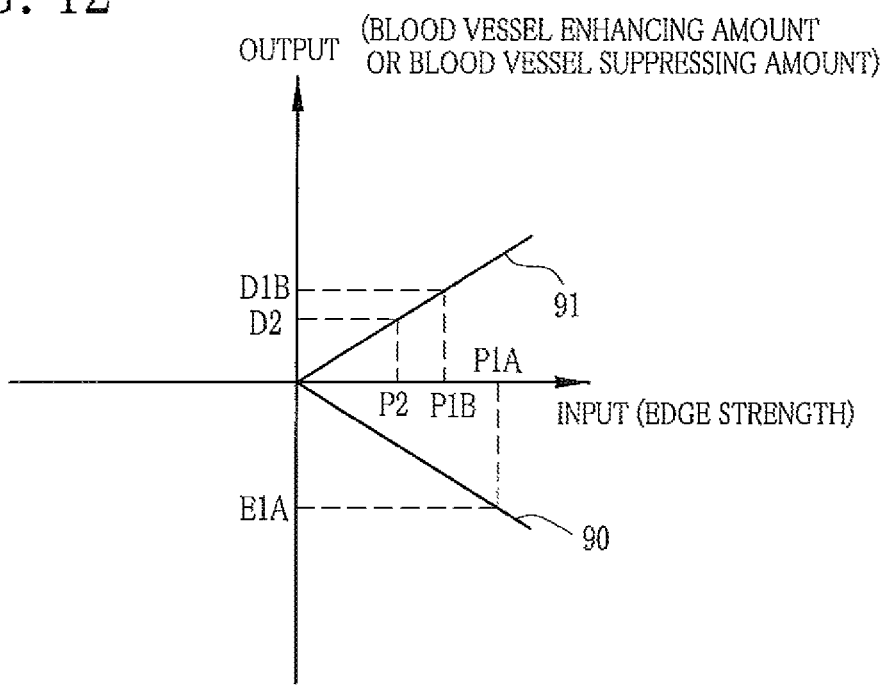
FIG. 12 is a graph showing the relation between edge strength and a blood vessel enhancing amount or a blood vessel suppressing amount.

The second display control image generator 84 produces a second display control image from the blood vessel extraction signal. The second display control image is used for selectively enhancing or suppressing display of the most superficial blood vessel C1A, the superficial blood vessel C1B, and the middle-layer blood vessel C2. The second display control image generator 84 sets an amount (enhancing amount or suppressing amount) for enhancing or suppressing each blood vessel in accordance with the edge strength of the blood vessel in the blood vessel extraction signal, and thereby produces the second display control image. The second display control image generator 84 has a lookup table (LUT) 84a for storing the relation between the edge strength and the enhancing amount or the suppressing amount of the blood vessel. The enhancing amount or the suppressing amount of each blood vessel is set with referring to the LUT 84a. Thus, the second display control image is obtained. As shown in FIG. 12, in a case where the blood vessel having an edge strength exceeding the threshold value P1B is enhanced and the blood vessel having an edge strength less than or equal to the threshold value P1B is suppressed, an input/output relation 90 is used for an input exceeding the threshold value P1B, while an input/output relation 91 is used for an input less than or equal to the threshold value P1B.

Accordingly, the input/output relation 90 is used for the most superficial blood vessel C1A since the edge strength P1A exceeds the threshold value P1B. According to the input/output relation 90, an enhancing amount E1A corresponding to the edge strength P1A is set. The input/output relation 91 is used for the superficial blood vessel C1B and the middle-layer blood vessel C2 since the edge strengths P1B and P2 are less than or equal to the threshold value P1B. According to the input/output relation 91, suppressing amounts D1B and D2, corresponding to the respective edge strengths P1B and P2, are set. Thus, the second display control image is produced by setting the enhancing amount E1A to the most superficial blood vessels C1A, the suppressing amount D1B to the superficial blood vessels C1B, and the suppressing amount D2 to the middle-layer blood vessel C2. Note that the input/output relation of the LUT is arbitrarily changeable by operation of the console 19 or the like.

The image superimposing unit 85 superimposes the first display control image on the base image to produce a first special image, in which the most superficial blood vessels C1A, the superficial blood vessels C1B, and the middle-layer blood vessel C2 are displayed separately or in a distinguishable manner. Also, the image superimposing unit 85 superimposes the second display control image on the base image to produce a second special image, in which the most superficial blood vessels C1A, the superficial blood vessels C1B, and the middle-layer blood vessel C2 are selectively enhanced or suppressed. The first and second display control images have an output value of "0" at a portion corresponding to the mucous membrane M, so that the mucous membrane M is neither enhanced nor suppressed in the case of superimposing the first or second display control image on the base image. Note that the image superimposing unit 85 adds the first or second display control image on the B image signal of the base image, but may add the first or second display control image on the G image signal or the R image signal of the base image.

Figure 11:
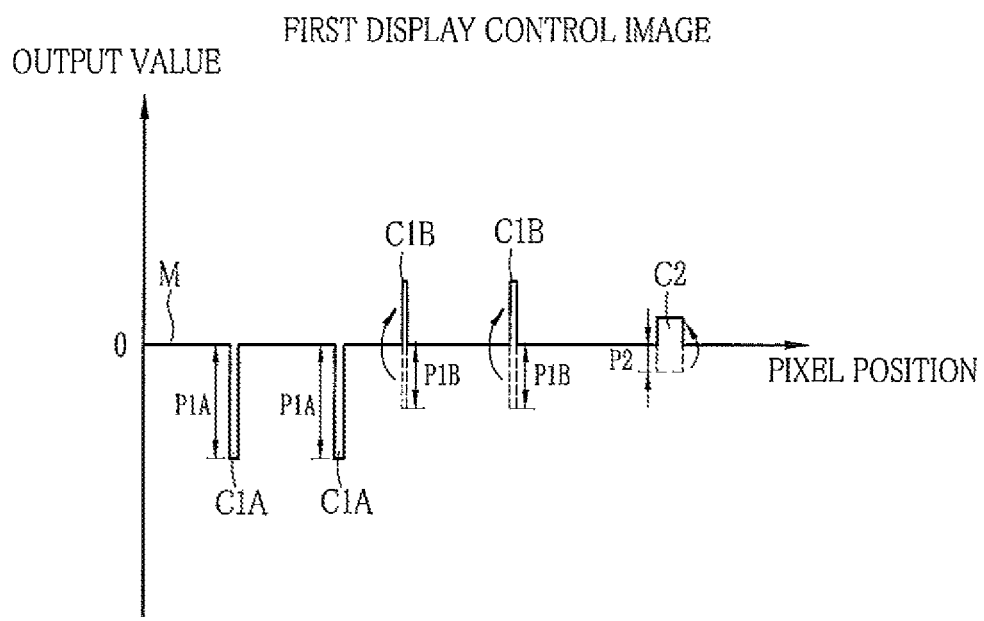
FIG. 11 is a graph showing the signal distribution of a first display control signal at the predetermined pixel line.
Figure 14:
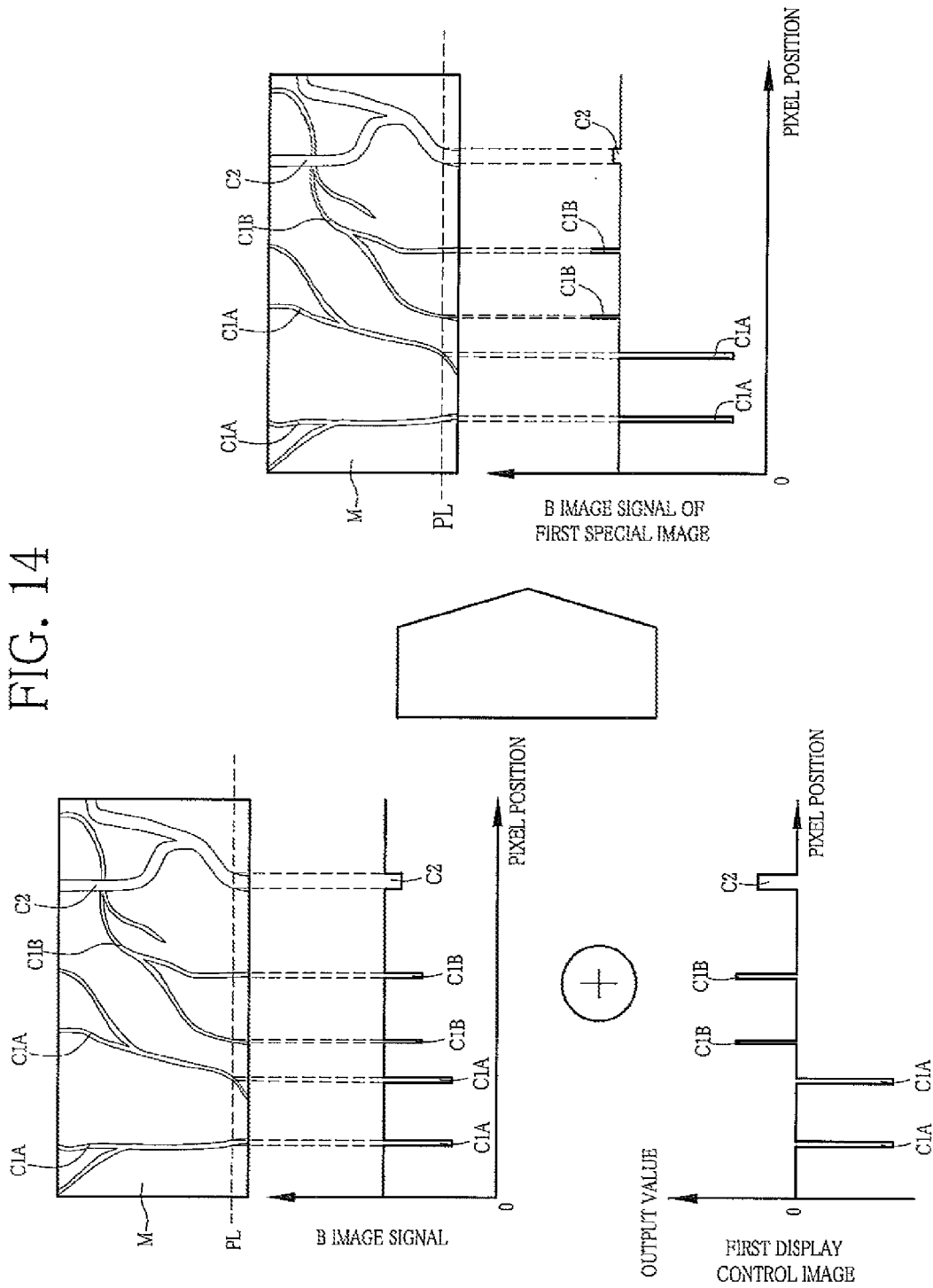
FIG. 14 is an explanatory view of a method for producing a first special image.

As shown in FIG. 14, taking the case of adding the first display control image of FIG. 11 to the B image signal of the base image of FIG. 8 as an example, the falling edges of the most superficial blood vessels C1A are maintained, while the falling edges of the superficial blood vessels C1B and the middle-layer blood vessel C2 are changed to the rising edges with increased output values. Thus, the first special image is obtained, in which the superficial blood vessels C1B and the middle-layer blood vessel C2 are brighter than the mucous membrane M. As described above, the most superficial blood vessels C1A, the superficial blood vessels C1B, and the middle-layer blood vessel C2 in the first special image are displayed separately by representing the most superficial blood vessels C1A as the falling edges and the superficial blood vessels C1B and the middle-layer blood vessel C2 as the rising edges. Note that the most superficial blood vessels C1A may be represented by rising edges and the superficial blood vessels C1B and the middle-layer blood vessel C2 may be represented by falling edges in the first special image instead.

Figure 13:
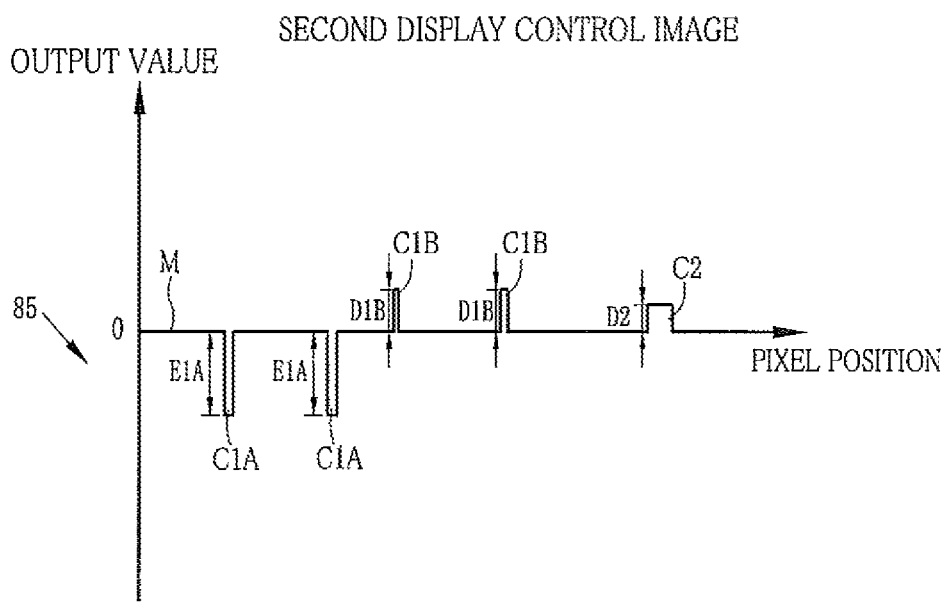
FIG. 13 is a graph showing the signal distribution of a second display control image at the predetermined pixel line.
Figure 15:
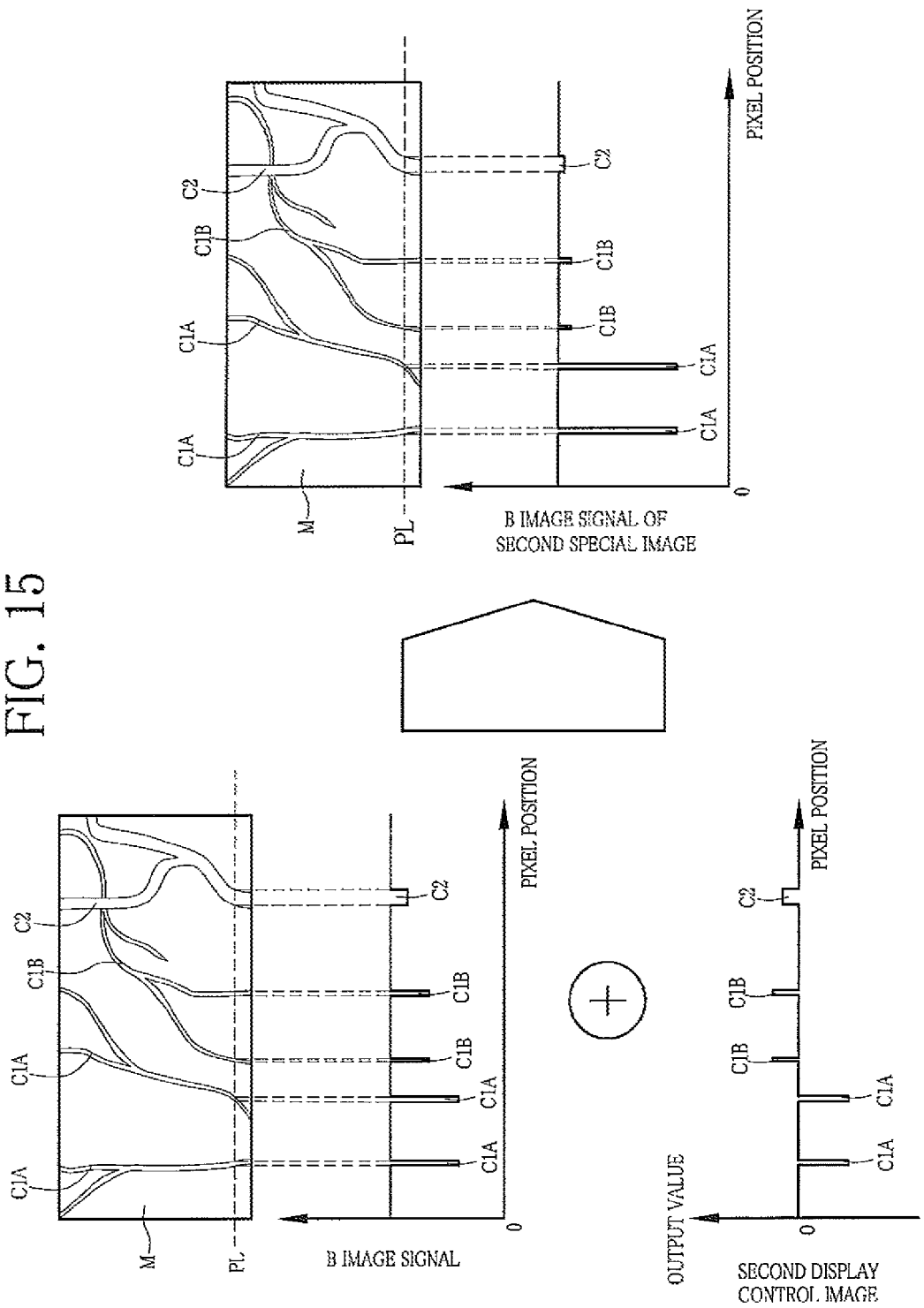
FIG. 15 is an explanatory view of a method for producing a second special image.

As shown in a second special image illustrated in FIG. 15, taking the case of adding the second display control image of FIG. 13 to the B image signal of the base image of FIG. 8 as an example, the most superficial blood vessels C1A have reduced pixel values and high contrast to the mucous membrane M due to the addition of the second display control image. Thus, the most superficial blood vessels C1A are enhanced in the display. On the other hand, the superficial blood vessels C1B and the middle-layer blood vessel C2 have increased pixel values and low contrast to the mucous membrane M due to the addition of the second display control image. Accordingly, the superficial blood vessels C1B and the middle-layer blood vessel C2 are suppressed in the display. Thus, the most superficial blood vessels C1A, the superficial blood vessels C1B, and the middle-layer blood vessel C2 are selectively enhanced or suppressed in the second special image.

The video signal generator 66 converts the RGB image signals of the normal image inputted from the normal image processing unit 62 and the RGB image signals of the first special image and the RGB image signals of the second special image inputted from the special image processing unit 64 into video signals displayable on the monitor 18. Based on the converted video signals, the monitor 18 displays the normal image in the normal observation mode, and the first special image or the second special image in the special observation mode.

Figure 16:
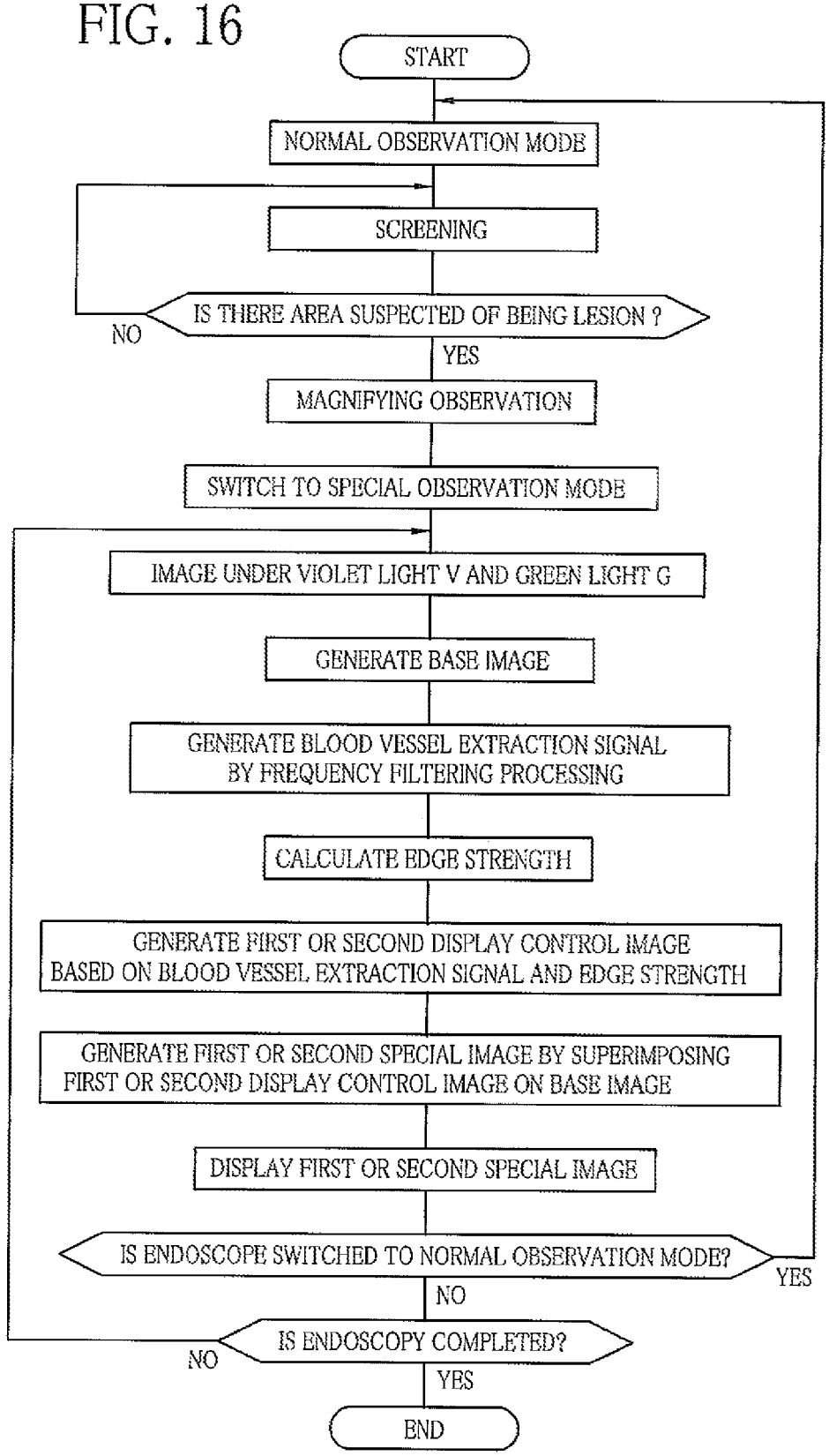
FIG. 16 is a flowchart showing a sequential flow of the present invention.

Next, the operation of the present invention will be described with referring to a flowchart of FIG. 16. First, in the normal observation mode, screening is performed from distant view (in a zoomed state). During the screening, if an area (lesion suspected area) suspected of being a lesion such as a brownish area or redness is detected, the zooming operation unit 13b is operated to magnify the display of the lesion suspected area. Thereby the magnified observation is performed. At the same time, the mode switch 13a is operated to put the endoscope system 10 into the special observation mode.

In the special observation mode, only the V-LED 20a and the G-LED 20c are turned on, so that the violet light V and the green light G are applied simultaneously to the lesion suspected area. The image sensor 48 captures an image of the lesion suspected area irradiated with the violet light V and the green light G. The image sensor 48 outputs the RGB image signals.

Based on the RGB image signals, the base image for use in display control of the most superficial blood vessel C1A, the superficial blood vessel C1B, and the middle-layer blood vessel C2 is produced. Also, the blood vessel extraction signal is produced by applying the frequency filtering processing to the B image signal. In the blood vessel extraction signal, the output value of the mucous membrane M is set to "0" and the output values of the most superficial blood vessel C1A, the superficial blood vessel C1B, and the middle-layer blood vessel C2 are set to "negative". The edge strengths of the most superficial blood vessel C1A, the superficial blood vessel C1B, and the middle-layer blood vessel C2 are calculated from the blood vessel extraction signal. Then, based on the blood vessel extraction signal and the edge strengths, the first or second display control image, which is used for controlling the display of the most superficial blood vessel C1A, the superficial blood vessel C1B, and the middle-layer blood vessel C2, is produced.

The first or second display control image is superimposed on or combined with the base image to produce the first or second special image. The first or second special image is displayed on the monitor 18. In the first special image, the most superficial blood vessel C1A, the superficial blood vessel C1B, and the middle-layer blood vessel C2 are displayed separately or in a distinguishable manner. In the second special image, the most superficial blood vessel C1A, the superficial blood vessel C1B, and the middle-layer blood vessel C2 are selectively enhanced or suppressed. The display of the first or second special image is maintained until the endoscope system 10 is switched to the normal observation mode by the operation of the mode switch 13a. Even if the endoscope system 10 is not switched to the normal observation mode, the endoscope 12 is pulled out of the body cavity and the display of the image on the monitor 18 is stopped after the endoscopic diagnosis is completed.

(Second Embodiment)

In the above first embodiment, the color image sensor captures the plurality of image signals necessary for each observation mode at a time. According to a second embodiment, a monochrome image sensor sequentially captures a plurality of image signals necessary for each observation mode, instead.

Figure 17:
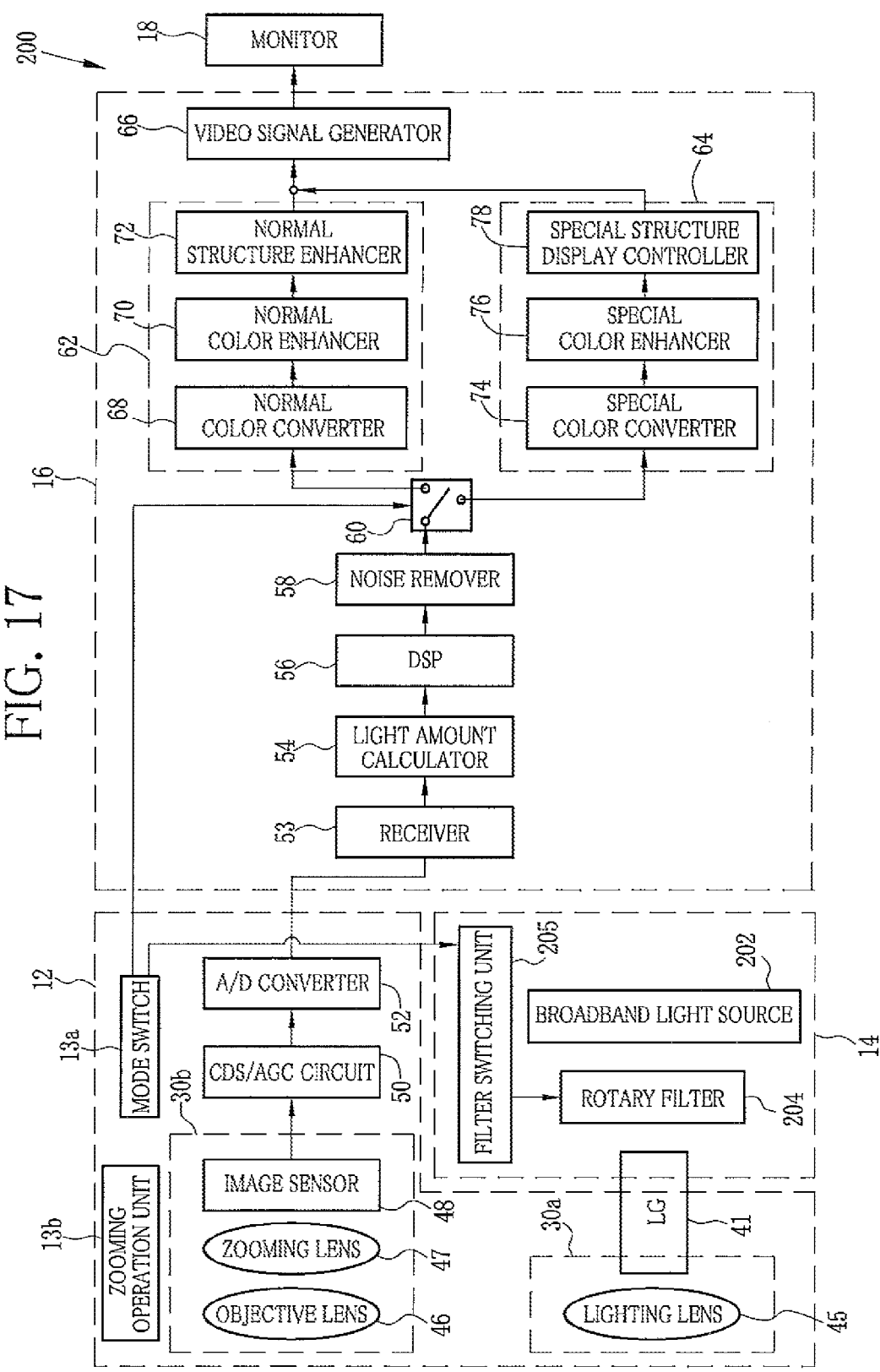
FIG. 17 is a block diagram showing the functions of an endoscope according to a second embodiment.

As shown in FIG. 17, the light source device 14 of an endoscope system 200 of a frame sequential type is provided with a broadband light source 202, a rotary filter 204, and a filter switching unit 205, instead of the V-LED 20a and the like. The imaging optical system 30b has a monochrome image sensor 206 without color filters, instead of the color image sensor 48. Other than those, the structure of the endoscope system 200 is the same as that of the endoscope system 10 according to the first embodiment.

The broadband light source 202, being a xenon lamp, a white LED, or the like, emits white light having a wavelength range from blue to red regions. The rotary filter 204 has an inner filter 208 for use in the normal observation mode and an outer filter 209 for use in the special observation mode (see FIG. 18). The filter switching unit 205 shifts the rotary filter 204 in its radial direction. In a case where the endoscope system 200 is put into the normal observation mode by the operation of the mode switch 13a, the filter switching unit 205 inserts the inner filter 208 into an optical path of the white light. In a case where the endoscope system 200 is put into the special observation mode, the filter switching unit 205 inserts the outer filter 209 into the optical path of the white light.

Figure 18:
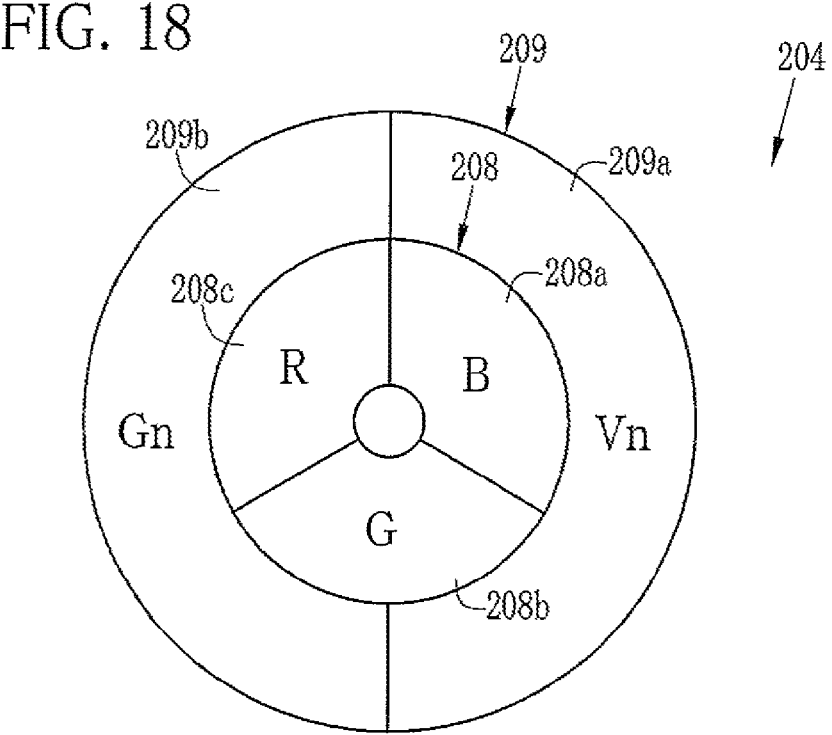
FIG. 18 is a plan view of a rotary filter.

Referring to FIG. 18, the inner filter 208 for use in the normal observation mode includes a B filter 208a for allowing blue light of the white light to pass through, a G filter 208b for allowing green light of the white light to pass through, and an R filter 208c for allowing red light of the white light to pass through. The B filter 208a, the G filter 208b, and the R filter 208c are provided in a circumferential direction. Thus, in the normal observation mode, the blue light, the green light, and the red light are applied sequentially to the observation object while the rotary filter 204 is rotated.

The outer filter 209 for use in the special observation mode includes a Vn filter 209a and a Gn filter 209b provided in the circumferential direction. The Vn filter 209a allows violet light V, which has a center wavelength of 405 nm and a wavelength range of 380 to 440 nm, of the white light to pass through. The Gn filter 209b allows green narrowband light Gn of 530 to 550 nm to pass through. Thus, in the special observation mode, the violet light V and the green narrowband light Gn are applied alternately to the observation object while the rotary filter 204 is rotated. Note that the broadband light source 202 and the Vn filter 209a of the rotary filter 204 constitute a violet light emitter of the present invention.

As for the endoscope system 200 of the frame sequential type, the monochrome image sensor 206 captures an image of the observation object whenever the blue light, the green light, or the red light is applied thereto. Thus, the RGB three-color image signals are obtained. Based on the RGB image signals, a normal image is produced in a like manner as the above first embodiment. In the special observation mode, on the other hand, the monochrome image sensor 206 captures an image of the observation object whenever the violet light V or the green narrowband light Gn is applied thereto. Thus, a B image signal and a Gn image signal (corresponding to the G image signal of the first embodiment) are obtained. Based on the B image signal and the Gn image signal, a first or second special image is produced in a like manner as the first embodiment.

(Third Embodiment)

In the above first and second embodiments, imaging is performed under irradiation with the violet light V and the green light G, and the B image signal and the G image signal corresponding to the violet light V and the green light G are obtained to produce the first or second special image. In a third embodiment, the B image signal and the G image signal corresponding to the violet light V and the green light G are obtained by spectral calculation based on a broadband image such as a white light image.

Figure 19:
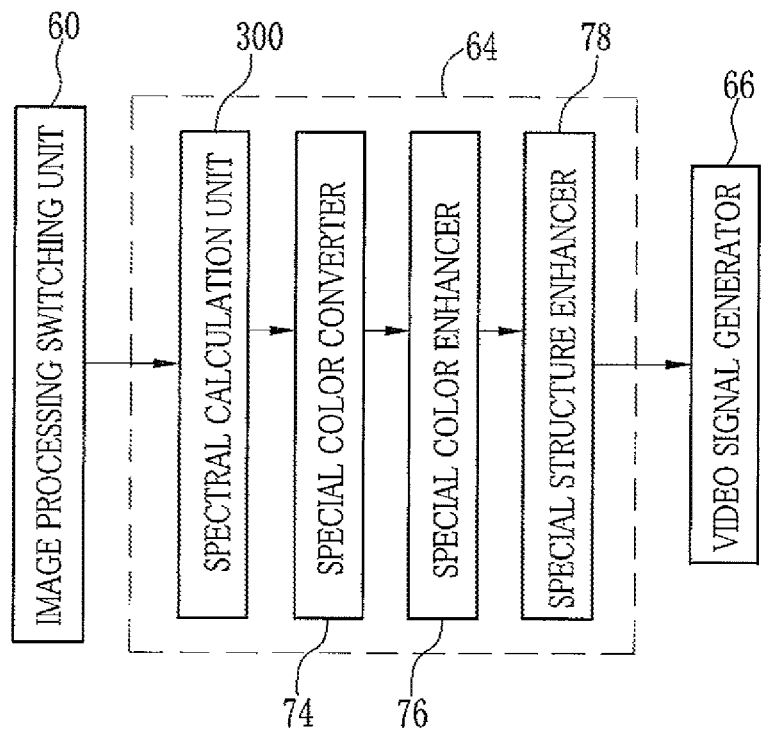
FIG. 19 is a block diagram showing the functions of a special image processing unit according to a third embodiment.

In this case, white light, being broadband light, is emitted from a broadband light source (corresponding to a white light emitter of the present invention) in the special observation mode of the endoscope system 10 according to the first embodiment. As shown in FIG. 19, the special image processing unit 64 is provided with a spectral calculation unit 300, which performs spectral calculation processing based on RGB image signals of a white light image captured under the white light. By the spectral calculation processing, a B image signal and a G image signal corresponding to violet light V (380 to 440 nm) and green light G (480 to 600 nm) included in reflected light of the white light are produced. According to the third embodiment, a first or second special image is produced based on the B image signal and the G image signal produced by the spectral calculation unit 300, in a manner similar to the first embodiment. Note that the white light may be generated by use of a phosphor, or broadband light emitted from a broadband light source such as a xenon lamp.

In the above first and second embodiments, the red light R, in addition to the violet light V and the green light G, may be applied in the special observation mode. In this case, all of the RGB image signals contain the information about the observation object including the blood vessels, so that the special color converter 74 applies color conversion processing, which is represented by the following conversion expressions (1') to (3'), to each of the RGB image signals.

$$\text{Color-converted } R \text{ image signal} = k1' \times R \text{ image signal} \quad (1')$$

$$\text{Color-converted } G \text{ image signal} = k2' \times G \text{ image signal} \quad (2')$$

$$\text{Color-converted } B \text{ image signal} = k3' \times B \text{ image signal} \quad (3')$$

Wherein, "k1'" to "k3'" are positive coefficients.

Figure 20:
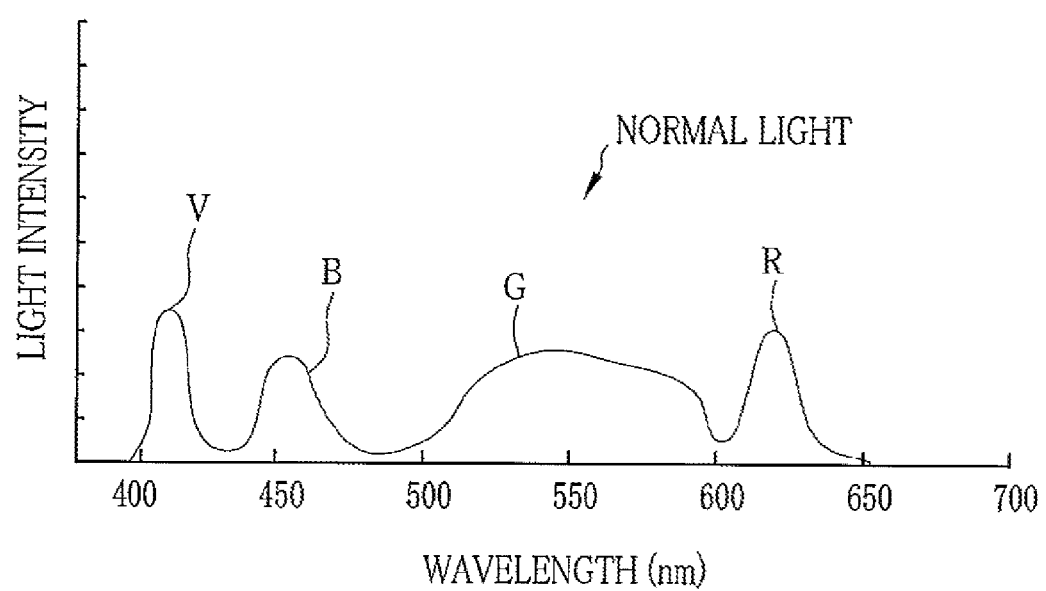
FIG. 20 is a graph showing an emission spectrum of normal light different from FIG. 3.

Note that, the light having the emission spectrums of FIGS. 3 and 4 is used in the first embodiment, but light having another spectrum may be used instead. For example, as shown in FIG. 20, the violet light V may be changed to light having a center wavelength of 410 to 415 nm and a wavelength range on a little longer wavelength side, and the blue light B may be changed to light having a center wavelength of 445 to 460 nm and a wavelength range on a little shorter wavelength side, while the green light G and the red light R are not changed. In this case, the upper limit of the wavelength range of the violet light V needs to be less than 440 nm to calculate the edge strength of each of the blood vessels C1A, C1B, and C2.

Note that, according to the above embodiments, the present invention is implemented during the endoscopic diagnosis. Alternatively, the present invention may be implemented after completion of the endoscopic diagnosis and based on an endoscopic image recorded in the storage of the endoscope system. The present invention may be applied to a capsule endoscopic image captured with a capsule endoscope.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
   an image signal generator for imaging a surface of mucous membrane of an observation object and producing color image signals composed of image signals of different colors;
   a base image generator for producing a base image based on the color image signals;
   a frequency filtering processing unit for applying frequency filtering processing to at least the image signal with a short wavelength of the color image signals and obtaining a blood vessel extraction signal in which blood vessels at different depths are extracted, wherein in the blood vessel extraction signal, the blood vessels are represented by falling edges having negative output values with respect to an output value at a portion corresponding to the mucous membrane, and an absolute value of the output value increases with decreasing blood vessel depth;
   an edge strength calculator for calculating edge strength of the each blood vessel based on the blood vessel extraction signal, wherein the edge strength increases with decreasing blood vessel depth, and at least one of the blood vessels at different depths exceeds a predetermined threshold edge strength value; and
   a special image generator for applying display control processing to the base image based on the edge strength of the each blood vessel and producing a special image in which a display of the each blood vessel is controlled, wherein the blood vessel having the edge strength less than the threshold edge strength value is changed from the falling edge to a rising edge in the display control processing.

2. The endoscope system according to claim 1, wherein the blood vessels in the blood vessel extraction signal include a first-layer blood vessel and a second-layer blood vessel located deeper than the first-layer blood vessel, and the first-layer blood vessel is represented by a falling edge with the edge strength exceeding a predetermined value, and the second-layer blood vessel is represented by a falling edge with the edge strength less than or equal to the predetermined value.

3. The endoscope system according to claim 2, wherein the special image is a first special image in which one of the first and second-layer blood vessels is represented by a falling edge and the other blood vessel is represented by a rising edge.

4. The endoscope system according to claim 3, wherein the first-layer blood vessel is represented by the falling edge and the second-layer blood vessel is represented by the rising edge in the first special image.

5. The endoscope system according to claim 4, the special image generator including:
   a first display control image generator for producing a first display control image from the blood vessel extraction signal, the falling edge of the second-layer blood vessel being changed to a rising edge in the first display control image; and
   an image superimposing unit for producing the first special image by adding the first display control image to the base image so that the second-layer blood vessel is represented by a rising edge in the first special image.

6. The endoscope system according to claim 2, wherein the special image is a second special image in which the first-layer and second-layer blood vessels are selectively enhanced or suppressed.

7. The endoscope system according to claim 6, the special image generator including:
   a second display control image generator for producing a second display control image based on the blood vessel extraction signal, an amount for enhancing or suppressing the each blood vessel being determined in accordance with the edge strength in the second display control image; and
   a second image superimposing unit for superimposing the second display control image on the base image and producing the second special image.

8. The endoscope system according to claim 2, wherein the first-layer blood vessel is a most superficial blood vessel and the second-layer blood vessel is a superficial blood vessel or a middle-layer blood vessel.

9. The endoscope system according to claim 1, wherein the image signal with the short wavelength corresponds to violet light having a wavelength range of 380 to 440 nm.

10. The endoscope system according to claim 9, further including:
    a violet light emitter for applying the violet light to the observation object, wherein the image signal with the short wavelength is obtained by imaging the observation object under the violet light.

11. The endoscope system according to claim 9, further including:
a white light emitter for applying white light to the observation object; and
a spectral calculation unit for performing spectral calculation based on a white light image of the observation object captured under the white light and thereby producing the image signal with the short wavelength.

12. The endoscope system according to claim 9, wherein the color image signals include the image signal with a long wavelength which corresponds to green light in a wavelength range of 480 to 600 nm or green narrowband light in a wavelength range of 530 to 550 nm, and the base image is produced based on the image signal with the short wavelength and the image signal with the long wavelength.

13. A processor device connected to an endoscope having an image signal generator for imaging a surface of mucous membrane of an observation object and producing color image signals composed of image signals of different colors, the processor device comprising:
a receiver for receiving the color image signals;
a base image generator for producing a base image based on the color image signals;
a frequency filtering processing unit for applying frequency filtering processing to at least the image signal with a short wavelength of the color image signals and obtaining a blood vessel extraction signal in which blood vessels at different depths are extracted, wherein in the blood vessel extraction signal, the blood vessels are represented by falling edges having negative output values with respect to an output value at a portion corresponding to the mucous membrane, and an absolute value of the output value increases with decreasing blood vessel depth;
an edge strength calculator for calculating edge strength of the each blood vessel based on the blood vessel extraction signal, wherein the edge strength increases with decreasing blood vessel depth, and at least one of the blood vessels at different depths exceeds a predetermined threshold edge strength value; and
a special image generator for applying display control processing to the base image based on the edge strength of the each blood vessel and producing a special image in which a display of the each blood vessel is controlled, wherein the blood vessel having the edge strength less than the threshold edge strength value is changed from the falling edge to a rising edge in the display control processing.

14. A method for operating an endoscope system comprising the steps of:
imaging a surface of mucous membrane of an observation object and producing color image signals composed of image signals of different colors, with an image signal generator;
producing a base image based on the color image signals, with a base image generator;
applying frequency filtering processing to at least the image signal with a short wavelength of the color image signals and obtaining a blood vessel extraction signal in which blood vessels at different depths are extracted, with a frequency filter processing unit, wherein in the blood vessel extraction signal, the blood vessels are represented by falling edges having negative output values with respect to an output value at a portion corresponding to the mucous membrane, and an absolute value of the output value increases with decreasing blood vessel depth;
calculating edge strength of the each blood vessel based on the blood vessel extraction signal, with an edge strength calculator, wherein the edge strength increases with decreasing blood vessel depth, and at least one of the blood vessels at different depths exceeds a predetermined threshold edge strength value; and
applying display control processing to the base image based on the edge strength of the each blood vessel and producing a special image in which a display of the each blood vessel is controlled, with a special image generator, wherein the blood vessel having the edge strength less than the threshold edge strength value is changed from the falling edge to a rising edge in the display control processing.

15. The endoscope system according to claim 1, further comprising a color enhancer for applying color enhancement processing to the color image signals, wherein the frequency filtering processing unit applies the frequency filtering processing to at least the image signal with a short wavelength of the color-enhanced image signals to obtain the blood vessel extraction signal.

* * * * *